United States Patent
Katsuno et al.

(10) Patent No.: US 9,522,251 B2
(45) Date of Patent: Dec. 20, 2016

(54) MOUNTING CARD

(71) Applicant: ASAHI INTECC CO., LTD., Nagoya-shi, Aichi (JP)

(72) Inventors: Ryota Katsuno, Tajimi (JP); Rin Take, Nagoya (JP)

(73) Assignee: ASAHI INTECC CO., LTD., Nagoya-shi (JP)

( * ) Notice: Subject to any disclaimer, the term of this patent is extended or adjusted under 35 U.S.C. 154(b) by 0 days.

(21) Appl. No.: 14/704,379

(22) Filed: May 5, 2015

(65) Prior Publication Data

US 2015/0320967 A1    Nov. 12, 2015

(30) Foreign Application Priority Data

May 10, 2014    (JP) .................................. 2014-098192

(51) Int. Cl.
  *A61M 25/00*    (2006.01)
  *B65D 73/00*    (2006.01)

(52) U.S. Cl.
  CPC ........ *A61M 25/002* (2013.01); *B65D 73/0014* (2013.01)

(58) Field of Classification Search
  CPC .............. B65D 73/0014; B65D 73/005; B65D 73/0021; A61M 25/002
  USPC .............. 206/364, 36.3, 363, 477–483, 495, 438,206/6.3
  See application file for complete search history.

(56) References Cited

U.S. PATENT DOCUMENTS

| | | | | |
|---|---|---|---|---|
| 2,224,027 | A * | 12/1940 | Tate ........................ | G09F 5/042 206/476 |
| 3,967,728 | A * | 7/1976 | Gordon ............... | A61M 25/002 206/210 |
| 4,023,678 | A * | 5/1977 | Fiedler ............... | B65D 73/0021 206/363 |
| 5,121,836 | A * | 6/1992 | Brown ............. | A61B 17/06138 206/438 |
| 5,127,518 | A * | 7/1992 | Holzwarth ....... | A61B 17/06138 206/63.3 |

(Continued)

FOREIGN PATENT DOCUMENTS

| | | |
|---|---|---|
| EP | 0 913 164 A1 | 5/1999 |
| JP | 2000255627 A | 9/2000 |

(Continued)

OTHER PUBLICATIONS

Jun. 9, 2015 Extended European Search Report in European Patent Application No. 15162879.9.

*Primary Examiner* — Steven A. Reynolds
(74) *Attorney, Agent, or Firm* — Oliff PLC

(57) ABSTRACT

A mounting card has a sufficient holding force for holding an elongated flexible medical component and prevents deformation and breakage of the flexible medical component when the flexible medical component is pulled out from the proximal end side of the mounting card. The mounting card has a flat surface for holding the elongated flexible medical component. The flat surface comprises a U-shaped distal-side tab and a proximal-side tab that are formed in a pair. Furthermore, a distal-side of the proximal-side tab is parallel with a proximal-side of the distal-side tab, and a distance between the distal side of the proximal-side tab and the proximal side of the distal-side tab is larger than the diameter of the flexible medical component.

3 Claims, 3 Drawing Sheets

(56) References Cited

U.S. PATENT DOCUMENTS

| | | | | |
|---|---|---|---|---|
| 5,131,537 A * | 7/1992 | Gonzalez | B65D 75/326 | 206/364 |
| 5,226,535 A * | 7/1993 | Rosdhy | A61B 17/06138 | 206/363 |
| 5,234,106 A * | 8/1993 | Transue | B65D 73/0021 | 206/349 |
| 5,307,924 A * | 5/1994 | Manosalva | A61B 17/0401 | 206/339 |
| 5,487,469 A * | 1/1996 | Roshdy | A61B 17/06138 | 206/363 |
| 5,501,341 A * | 3/1996 | Van Es | A61M 25/002 | 206/364 |
| 5,788,063 A * | 8/1998 | Van Ness | A61B 17/06138 | 206/380 |
| 6,080,184 A * | 6/2000 | Peters | A61B 17/06133 | 206/63.3 |
| 6,871,740 B1 * | 3/2005 | Cao | A61M 25/0075 | 206/364 |
| 2005/0194276 A1 * | 9/2005 | Lubs | A61M 25/002 | 206/364 |
| 2010/0025273 A1 * | 2/2010 | Matsuda | A61M 25/002 | 206/370 |

FOREIGN PATENT DOCUMENTS

| | | |
|---|---|---|
| JP | 2007-527295 A | 9/2007 |
| JP | 2009-201826 A | 9/2009 |
| WO | 2005/087302 A1 | 9/2005 |

* cited by examiner

MOUNTING CARD

CROSS REFERENCE TO RELATED APPLICATION

This application claims priority to Japanese Patent Application No. 2014-098192 filed in the Japan Patent Office on May 10, 2014, the entire contents of which are incorporated herein by reference.

BACKGROUND

The disclosed embodiments relate to a mounting card.

Traditionally, a flexible medical component, such as a catheter, is typically held on a mounting card that has a flat surface and that is packaged in a sterile condition. The mounting card also has a plurality of tabs for holding the flexible medical component (such as the catheter). The tabs are formed by making cuts such as a V-shaped cut or a U-shaped cut on the mounting card. Furthermore, the tabs are slightly lifted from the flat surface of the mounting card and the flexible medical component is placed between the flat surface of the mounting card and the tabs so that the flexible medical component is held on the mounting card. However, if a holding force of the tab (a force for returning the tab to the flat surface) is small, a force for holding the flexible medical component becomes insufficient. If the holding force of the tab (the force for returning the tab to the flat surface) is large, another problem arises such that it becomes hard to remove a packaged flexible medical component from a package in order to use the flexible medical component. If the flexible medical component is an elongated component, the proximal side of the component is often held on the mounting card and the component must be pulled out from the package when the component is removed from the package. In this case, if a distal portion of the component is not linear (for example, a catheter having a curved distal portion), the distal portion of the component may be caught by the tab, which may cause deformation or breakage of the distal portion of the component.

For example, Patent Literature 1 (National Publication of Translated Version No. 2007-527295) discloses a mounting card having a flat surface that holds an elongated flexible medical component, e.g., a catheter. The flat surface has relatively large tabs and relatively small tabs in pairs that hold the component. The relatively large tabs and the relatively small tabs are formed by making triangular cuts with rounded tips on the mounting card. The tabs are shaped in pairs to reduce damage to the flexible medical component when the flexible medical component is removed from the mounting card.

Patent Literature 2 (Japanese Patent Laid-Open No. 2009-201826) discloses a mounting card that has a flat surface for holding an elongated flexible medical component, e.g., a catheter. The flat surface has pairs of L-shaped or mountain-shaped tabs that hold the flexible medical component. The L-shaped or mountain-shaped tabs are formed by making cuts on a mounting card. Additionally, cuts on both ends of the tabs, toward the distal end side of the flexible medical component, reduce a pulling resistance of the flexible medical component.

As described above, traditionally, mounting cards with tab cutouts have been used so as to prevent damage to a flexible medical component by producing a small pulling resistance, even in a case when the flexible medical component is pulled out from the mounting card.

However, flexible medical components have various shapes, and there is a need for a mounting card that can be used with different shaped flexible medical components. Furthermore, there is a need for a mounting card that has a sufficient holding force for holding the flexible medical component and preventing deformation or breakage to the flexible medical component, even when the flexible medical component is pulled out from the mounting card.

SUMMARY

The disclosed embodiments include a mounting card having a flat surface for holding an elongated flexible medical component, the mounting card having a sufficient holding force for holding the flexible medical component and preventing deformation or breakage of the flexible medical component even if the flexible medical component is pulled from its proximal side.

In certain embodiments, a mounting card is provided having a flat surface for holding an elongated flexible medical component. The flat surface comprises a U-shaped distal-side tab and a proximal-side tab. The distal-side tab and the proximal-side tab are formed in a pair so as to hold the flexible medical component on the flat surface. The distal-side tab is located closer to the distal end side of the flexible medical component than the proximal-side tab when the flexible medical component is held on the mounting card. The distal-side tab is formed by making a U-shaped cut on the mounting card such that a tip of the distal-side tab is oriented toward the distal end side of the flexible medical component when the flexible medical component is held on the mounting card. The proximal-side tab is formed by making a cut on the mounting card such that a distal side of the proximal-side tab is parallel with a proximal side of the distal-side tab. A distance between the distal side of the proximal-side tab and the proximal side of the distal-side tab is larger than a diameter of the flexible medical component.

The proximal-side tab may be formed by making a V-shaped cut on the mounting card.

According to the disclosed embodiments, even if a flexible medical component having a curved distal portion is held on the mounting card, the curved distal portion is not caught when the flexible medical component is pulled out from the mounting card. Thus, deformation or breakage of the flexible medical component is avoided when the flexible medical component is pulled out from the mounting card. Furthermore, the flexible medical component is reliably held by the distal-side tab and the proximal-side tab with an excellent holding force.

In some embodiments, the proximal-side tab is V-shaped and the proximal-side tab has a long base on which the mounting card and the proximal-side tab are not separated from each other. This provides an excellent holding force for holding the flexible medical component without excessively increasing the size of the proximal-side tab, and a sufficient holding force for holding the flexible medical component is easily obtained.

DETAILED DESCRIPTION OF THE EMBODIMENTS

Figure 1:
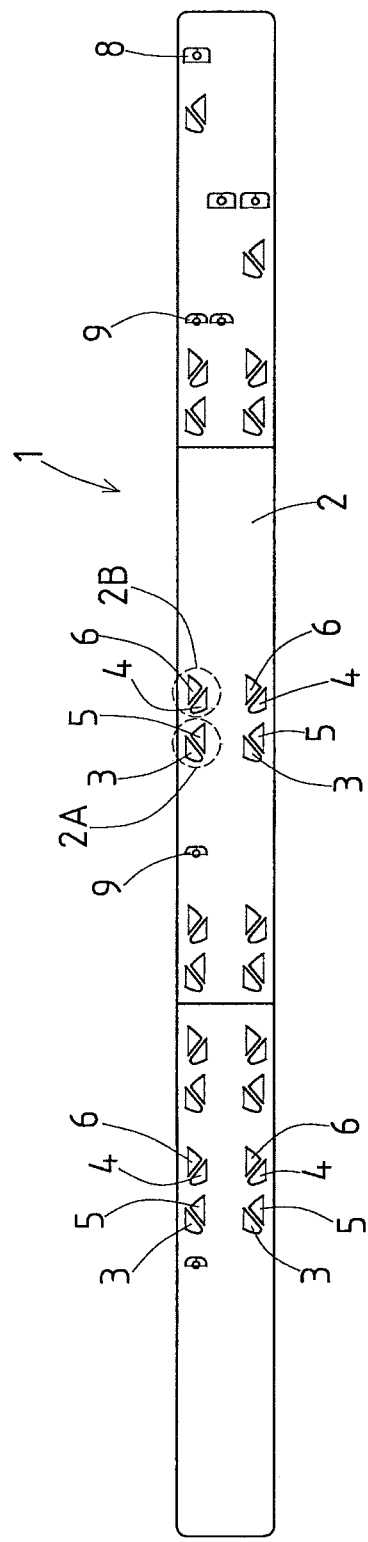
FIG. 1 is a front view schematically illustrating a mounting card according to embodiments.
Figure 2A:
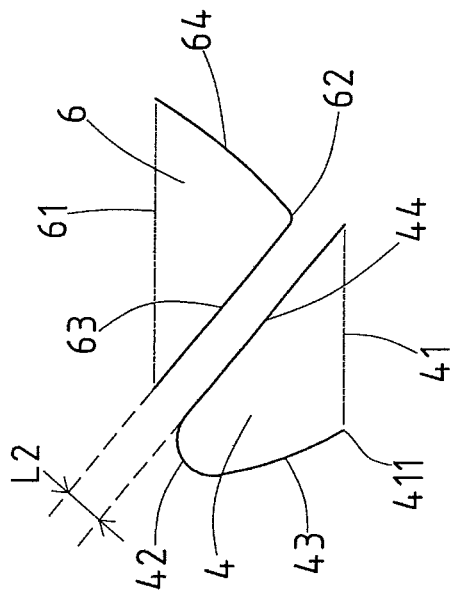
FIG. 2A is an enlarged view of part 2A of the mounting card of FIG. 1.
Figure 2B:
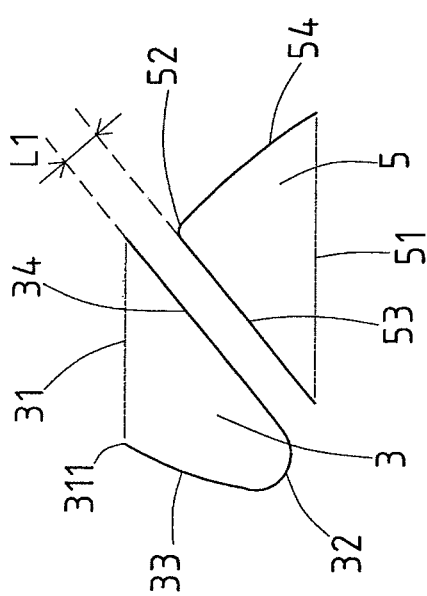
FIG. 2B is an enlarged view of part 2B of the mounting card of FIG. 1.

As shown in FIG. 1, a mounting card 1 has a flat surface 2 on which distal-side tabs 3 and 4 and proximal-side tabs 5 and 6 are formed. The distal-side tabs 3 and 4 and the proximal-side tabs 5 and 6 are formed by making cuts on the flat surface 2 with, for example, a cutter. The distal-side tabs 3 and 4 may each face toward different directions. The distal-side tab 3 has a tab base 31, which is not separated from the flat surface 2 and which is located on an upper side of distal-side tab 3, as shown in FIG. 2A. The distal-side tab 4 has a tab base 41, which is not separated from the flat surface 2 and which is located on a lower side of distal-side tab 4, as shown in FIG. 2B. Similarly, the proximal-side tab 5 and the proximal-side tab 6 may each face toward different directions. The proximal-side tab 5 has a tab base 51, which is not separated from the flat surface 2 and which is located on a lower side of proximal-side tab 5, as shown in FIG. 2A. The proximal-side tab 6 has a tab base 61, which is not separated from the flat surface 2 and which is located on an upper side of proximal-side tab 6, as shown in FIG. 2B. The distal-side tabs 3 and 4 and the proximal-side tabs 5 and 6 are formed such that the distal-side tab 3 and the proximal-side tab 5 are formed in a pair, so as to hold a flexible medical component 7, while the distal-side tab 4 and the proximal-side tab 6 are formed in a pair, so as to also hold the flexible medical component 7. Thus, the pair of tabs 3 and 5 may sufficiently hold the flexible medical component 7. Additionally, the pair of tabs 4 and 6 may also sufficiently hold the flexible medical component 7. Only one of the pairs (either tabs 3 and 5 or tabs 4 and 6) may be formed on the flat surface 2. However, both of the pairs may be formed on the flat surface 2 so that the flexible medical component may be held with the pair of tabs 3 and 5 and/or held with the pair of tabs 4 and 6, depending on the shape and size of the flexible medical component 7.

Figure 3:
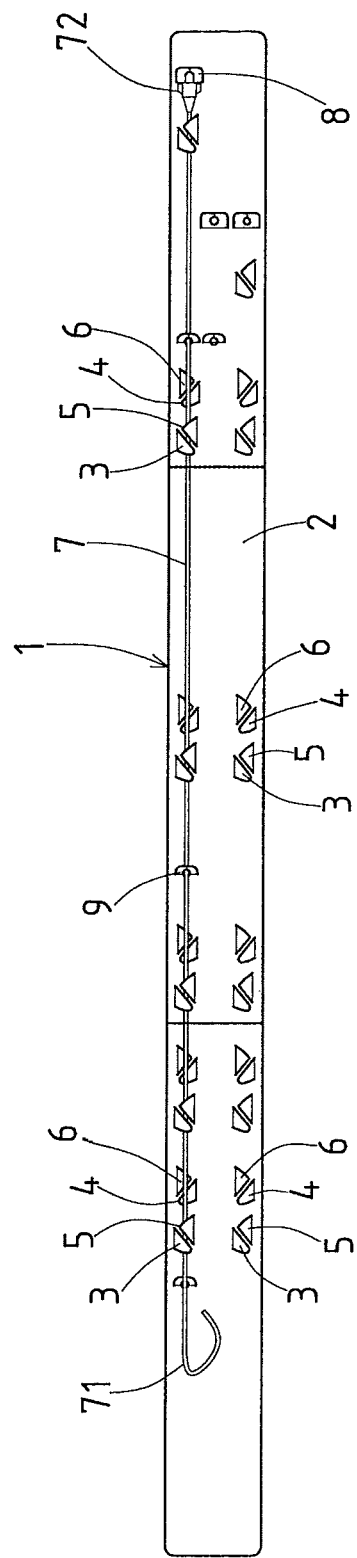
FIG. 3 is a front view schematically illustrating the mounting card of FIG. 1 with a flexible medical component.

The shape and size of the mounting card 1 is not particularly limited as long as the mounting card 1 is sufficient to hold the flexible medical component. For example, if the elongated flexible medical component 7 is a catheter, the mounting card 1 may be a rectangular sheet that is longer than the catheter. The mounting card 1 is preferably sized and shaped so as to hold the entire flexible medical component 7. However, the mounting card 1 may be sized and shaped so as to hold only a part of the flexible medical component 7. FIG. 3 shows a state in which the elongated flexible medical component 7 (e.g., a catheter) is held on the mounting card 1. As shown in FIG. 3, the mounting card 1 may be a rectangular sheet that can hold the entire flexible medical component 7. The flexible medical component 7 may be placed on the flat surface 2 and held between the flat surface 2 and the distal-side tab 3 and proximal-side tab 4.

The material of the mounting card 1 is not particularly limited and includes various traditional materials, such as paper, resin, and/or resin foam.

In some embodiments, the flat surface 2 is not precisely flat as long as the flexible medical component 7 can be placed on the mounting card 1.

The distal-side tabs 3 and 4 may be U-shaped with smooth (rounded) tips 32 and 42 and are located closer to the distal end side than the proximal-side tabs 5 and 6, which are arranged in pairs with the distal-side tabs 3 and 4. The U-shape may include, as shown in FIGS. 1 to 3, for example, a shape of a deformed letter U.

The distal-side tabs 3 and 4 may be formed by making U-shaped cuts on the mounting card 1 such that the tips 32 and 42 of the distal-side tabs 3 and 4 are oriented toward (extend toward) the distal end side. Because the tips 32 and 42 are oriented toward the distal end side, the tips 32 and 42 are located closer to the distal end side than distal ends 311 and 411 of the tab bases 31 and 41 in the axial direction of the flexible medical component 7 that is held by the mounting card 1.

The distal-side tabs 3 and 4 have distal sides 33 and 43, and the distal sides 33 and 43 may be linear or smoothly curved. The distal-side tabs 3 and 4 have proximal sides 34 and 44, and the proximal sides 34 and 44 may be linear or smoothly curved. In some embodiments, the proximal sides 34 and 44 are linear in view of the adjustability of a positional relationship with distal sides 53 and 63 of the proximal-side tabs 5 and 6, which will be described later.

Due to the shape of the distal-side tabs 3 and 4, the flexible medical component 7 held on the mounting card 1 can be removed from the mounting card 1 without a curved distal portion 71 of the flexible medical component 7 catching on the distal-side tabs 3 and 4. Thus, the flexible medical component 7 is not deformed or broken by the distal-side tabs 3 and 4 when removed from the mounting card 1.

The proximal-side tab 5 is located closer to the proximal end side than the distal-side tab 3, and the proximal-side tab 6 is located closer to the proximal end side than the distal-side tab 4.

The proximal-side tabs 5 and 6 may be arranged such that the distal sides 53 and 63 are parallel with the proximal sides 34 and 44 of the distal-side tabs 3 and 4. Therefore, in some embodiments, proximal sides 34 and 44 of the distal-side tabs 3 and 4 and the distal sides 53 and 63 of the proximal-side tabs 5 and 6 are all linear. This linear relationship allows the positional relationship between the proximal sides 34 and 44 of the distal-side tabs 3 and 4 and the distal sides 53 and 63 of the proximal-side tabs 5 and 6 to be easily adjusted. In other embodiments, the proximal sides 34 and 44 of the distal-side tabs 3 and 4 and the distal sides 53 and 63 of the proximal-side tabs 5 and 6 are all curved.

The proximal-side tabs 5 and 6 and the distal-side tabs 3 and 4 may be formed such that the distal sides 53 and 63 of the proximal-side tabs 5 and 6 and the proximal sides 34 and 44 of the distal-side tabs 3 and 4 are parallel with each other. Additionally, a distance between the distal sides 53 and 63 and the proximal sides 34 and 44 may be larger than the diameter of the flexible medical component 7. Specifically, a distance L1 between the distal side 53 of the proximal-side tab 5 and the proximal side 34 of the distal-side tab 3 and a distance L2 between the distal side 63 of the proximal-side tab 6 and the proximal side 44 of the distal-side tab 4, as shown in FIGS. 2A and 2B, may be larger than the diameter of the flexible medical component 7.

The tips 52 and 62 of the proximal-side tabs 5 and 6 may have V-shapes or smoothly curved U-shapes. The V-shapes of the tips 52 and 62 provide a long length from the base 51 and 61 to the tip 52 and 62, so that it is easier to hold the flexible medical component 7. The V-shaped tips 52 and 62 may also have slightly rounded corners to prevent the tips 52 and 62 from sticking in an operator's hand and, thus, to prevent the tips 52 and 62 from being damaged. For example, the V-shaped tips 52 and 62 may prevent the tips from sticking to the film of a package when the flexible medical component 7 is held and packaged.

The proximal-side tabs 5 and 6 have proximal sides 54 and 64, which may be linear or smoothly curved. In order to improve the holding force of the proximal-side tabs 5 and 6, that is, the force for holding the flexible medical component 7, the proximal-side tabs 5 and 6 preferably have large surface areas and have the long tab bases 51 and 61. The proximal sides 54 and 64 of the proximal-side tabs 5 and 6 are preferably linear so that the lengths of the tab bases 51 and 61 can be secured while keeping the large surface areas of the proximal-side tabs 5 and 6.

Thus, the proximal-side tabs 5 and 6 preferably include, in some embodiments, the linear distal sides 53 and 63, the linear proximal sides 54 and 64, and the V-shaped tips 52 and 62.

The proximal-side tabs 5 and 6 can reliably hold the flexible medical component 7. Moreover, when the flexible medical component 7 with the curved distal portion 71 is held on the mounting card 1 and then removed from the mounting card 1, the distal portion 71 of the flexible medical component 7 is not caught by the proximal-side tabs 5 and 6. Thus, the flexible medical component 7 is not deformed or broken by the distal-side tabs 3 and 4 when the flexible medical component 7 is removed from the mounting card 1.

The flat surface 2 of the mounting card 1 may optionally have tabs in addition to the distal-side tabs 3 and 4 and the proximal-side tabs 5 and 6. These additional tabs may be shaped similar to the distal-side tabs 3 and 4 and to the proximal-side tabs 5 and 6, or have other shapes.

For example, the flat surface 2 may include a tunnel-like tab 8, as shown in FIGS. 1 and 3, that has a through hole for holding a bulky connector 72, which is typically attached to the proximal end side of the flexible medical component 7. Additionally or alternatively, the flat surface 2 may include a positioning tab 9 that suppresses a displacement of the holding position of the flexible medical component 7 on the flat surface 2.

The flexible medical component 7 may be a catheter, a sheath, etc. The distal portion 71 of the flexible medical component 7 may be curved. The mounting card 1 is suitable for holding catheters typically provided with a curved distal portion.

A method of using the mounting card 1 will be described below. The elongated flexible medical component 7 may be held by the tunnel-like tab 8 and the positioning tab 9. The distal-side tabs 3 and 4 and the proximal-side tabs 5 and 6 are lifted to hold the flexible medical component 7 between the flat surface 2 and the distal-side tabs 3 and 4 and the proximal-side tabs 5 and 6. The flexible medical component 7 is thus held and secured on the flat surface 2 of the mounting card 1.

Embodiments of the present disclosure include a mounting card 1 that includes both distal-side tabs 3 and 4 and proximal-side tabs 5 and 6 or a mounting card 1 that includes only some, but not all of the tabs 3, 4, 5, and 6 (for example, only tabs 3 and 5 or only tabs 4 and 6).

In some embodiments, if the flexible medical component 7 having the curved distal portion 71 is held by the mounting card 1, distal tabs facing toward the same direction as the curving direction of the distal portion 71 may be used. In FIG. 3, the flexible medical component 7 includes the distal portion 71 that is curved downward so that, in some embodiments, the distal-side tab 3 (which faces downward in the same direction as the curving direction of the distal portion 71), and the proximal-side tab 5 may be used. In other words, the flexible medical component 7 having the distal portion 71 that is curved downward is held by the pairs that include the distal-side tabs 3 and the proximal-side tabs 5. In this case, the pairs that include the distal-side tabs 4 and the proximal-side tabs 6 are not used.

After the flexible medical component 7 is held on the mounting card 1, the mounting card with the flexible medical component 7 is packaged into a packaging bag according to a conventional method. The flexible medical component 7 may then be optionally sterilized.

In use, the packaging bag may be opened by, for example, a doctor to remove the flexible medical component 7 from the package for the use of the flexible medical component 7. When the flexible medical component 7 is removed, typically, the mounting card 1 with the flexible medical component 7 is removed from the packaging bag and then the flexible medical component 7 is carefully detached from the mounting card 1. Because the flexible medical component 7 is long, users tend to open the packaging bag at the proximal end side of the flexible medical component 7 and pull out the flexible medical component 7 from the packaging bag and from the mounting card 1. The mounting card 1, according to the embodiments disclosed herein, advantageously prevents and/or reduces the flexible medical component from being deformed or broken when the flexible medical component 7 is pulled out from the mounting card 1.

What is claimed is:

1. A mounting card comprising:
a flat surface configured to hold an elongated flexible medical component, wherein:
the flat surface comprises a U-shaped distal-side tab and a proximal-side tab, the distal-side tab and the proximal-side tab being formed in a pair so as to hold the flexible medical component against the flat surface,
the distal-side tab includes a tip and a base, the base including a first end and a second end such that the first end is located distally of the second end in a longitudinal direction,
the tip is disposed distally of the first end in the longitudinal direction such that a center axis of the tip is offset from a center axis of the first end, the center axis of the tip and the center axis of the first end being perpendicular to the longitudinal direction,
a distal side of the proximal-side tab is parallel to a proximal side of the distal-side tab, and
a distance between the distal side of the proximal-side tab and the proximal side of the distal-side tab is larger than a diameter of the flexible medical component.

2. The mounting card according to claim 1, wherein the proximal-side tab is formed by making a V-shaped cut on the mounting card.

3. The mounting card according to claim 1, further comprising a second distal-side tab and a second proximal-side tab that are both disposed proximal to the distal-side tab and to the proximal-side tab,
the second distal-side tab including a tip and a base, the base of the second-distal side tab including a first end and a second end such that the first end of the second-distal side tab is located distally of the second end of the second-distal side tab in the longitudinal direction, and
the tip of the second-distal side tab being disposed distally of the first end of the second-distal site tab in the longitudinal direction such that a center axis of the tip of the second-distal side tab is offset from a center axis of the first end of the second-distal side tab, the center axis of the tip of the second-distal side tab and the center axis of the first end of the second-distal side tab being perpendicular to the longitudinal direction.

* * * * *